US 7,498,341 B2

(12) United States Patent
Defossa et al.

(10) Patent No.: US 7,498,341 B2
(45) Date of Patent: Mar. 3, 2009

(54) HETEROCYCLICALLY SUBSTITUTED 7-AMINO-4-QUINOLONE-3-CARBOXYLIC ACID DERIVATIVES, PROCESS FOR THEIR PREPARATION AND THEIR USE AS MEDICAMENTS

(75) Inventors: Elisabeth Defossa, Idstein (DE); Dieter Kadereit, Offenbach (DE); Sven Ruf, Florsheim (DE); Thomas Klabunde, Frankfurt (DE); Dieter Schmoll, Frankfurt (DE); Andreas Herling, Bad Camberg (DE); Karl-Ulrich Wendt, Frankfurt (DE)

(73) Assignee: Sanofi Aventis Deutschland GmbH, Frankfurt (DE)

( * ) Notice: Subject to any disclaimer, the term of this patent is extended or adjusted under 35 U.S.C. 154(b) by 405 days.

(21) Appl. No.: 11/042,589

(22) Filed: Jan. 25, 2005

(65) Prior Publication Data

US 2005/0182086 A1    Aug. 18, 2005

Related U.S. Application Data

(60) Provisional application No. 60/582,416, filed on Jun. 24, 2004.

(30) Foreign Application Priority Data

Jan. 31, 2004    (DE) .................. 10 2004 004 972

(51) Int. Cl.
*A61K 31/4375*    (2006.01)
(52) U.S. Cl. ...................... 514/300; 546/123
(58) Field of Classification Search ............ 546/122, 546/123; 514/300
See application file for complete search history.

(56) References Cited

U.S. PATENT DOCUMENTS

| 5,153,203 | A * | 10/1992 | Yatsunami et al. ......... 514/312 |
| 6,221,633 | B1 | 4/2001 | Ertl et al. |
| 6,221,897 | B1 | 4/2001 | Frick et al. |
| 6,245,744 | B1 | 6/2001 | Frick et al. |
| 6,342,512 | B1 | 1/2002 | Kirsch |
| 6,624,185 | B2 | 9/2003 | Glombik |
| 6,967,205 | B1 * | 11/2005 | Abdul-Rahman ........... 514/291 |
| 7,129,249 | B2 * | 10/2006 | Birch et al. ................ 514/300 |

FOREIGN PATENT DOCUMENTS

| DE | 10142734 | | 3/2003 |
| EP | 0 462 884 | B1 | 6/1993 |
| ES | 2003196 | * | 10/1988 |
| JP | 61218586 | A * | 9/1986 |
| JP | 01165584 | A * | 6/1989 |
| WO | WO 9116311 | A1 * | 10/1991 |
| WO | WO 97/26265 | | 7/1997 |
| WO | WO 97/41097 | | 11/1997 |
| WO | WO 98/08871 | | 3/1998 |
| WO | WO 99/03861 | | 1/1999 |
| WO | WO 99/15525 | | 4/1999 |
| WO | WO 00/40569 | | 7/2000 |
| WO | WO 00/63208 | | 10/2000 |
| WO | WO 00/64876 | | 11/2000 |
| WO | WO 00/64888 | | 11/2000 |
| WO | WO 00/66585 | | 11/2000 |
| WO | WO 00/71549 | | 11/2000 |
| WO | WO 00/78312 | | 12/2000 |
| WO | WO 01/09111 | | 2/2001 |
| WO | WO 01/83451 | | 11/2001 |
| WO | WO 01/85695 | | 11/2001 |
| WO | WO 01/91752 | | 12/2001 |
| WO | WO 03/010147 | A1 | 2/2003 |
| WO | WO 03/074513 | A2 | 9/2003 |

OTHER PUBLICATIONS

Nam, Keun-Soo; et. al. "Synthesis of quinolone antimicrobial agents and their antibacterial activities." Korean Journal of Medicinal Chemistry, 1995, 5(1), 2-5 (abstract only).*
Frank, K. E. et. al. "A simple, inexpensive apparatus for performance of preparative scale solution phase multiple parallel synthesis of drug analogs. I. Preparation of a retrospective library of quinolone antiinfective agents." Combinatorial Chemistry and High Throughput Screening, 1998, 1, 73-87 (abstract only).*
Yan, Ligang et. al. "Synthesis and antibacterial activity of 7-substituted-1-ethyl(2-fluoro-ethyl)-6,8-difluoro-1,4-dihydro-4-oxo-quinoline-3-carboxylic acid." Yaoxue Xuebao, 1998, 33(5), 392-395 (abstract only).*

(Continued)

*Primary Examiner*—Rita J Desai
*Assistant Examiner*—David K O'Dell
(74) *Attorney, Agent, or Firm*—Barbara E. Kurys

(57) ABSTRACT

The invention relates to heterocyclically substituted 7-amino-4-quinolone-3-carboxylic acid derivatives and to the physiologically tolerated salts and physiologically functional derivatives thereof.

The invention relates to compounds of the formula I

[Chemical structure: quinolone derivative with substituents R1-R8 and X]

in which the radicals have the stated meanings, and to the physiologically tolerated salts thereof. The compounds are suitable for example as medicaments for the prevention and treatment of type 2 diabetes.

5 Claims, No Drawings

OTHER PUBLICATIONS

Nagibina, et. al. "Molecular rearrangements of 1,2,3-triazolines, 7-azido-6-fluoroquinolin-4-one adducts with alkenes." Russian Journal of Organic Chemistry 1998, 34(3), 434-446 (abstract only).*

Khalil, O. M. et. al. "New 7-substituted fluoroquinolones." Bulletin of the Faculty of Pharmacy (Cairo University), 2002, 40, 89-96 (abstract only).*

By Sardesai, K. S.; Sunthankar, S. V. "Biquinoline series. I. Synthesis of substituted 6,6'-biquinolines from diethyl ethoxymethylenemalonate." J. Sci. Ind. Research. (India), 1958, 17B, 269-72 (abstract only).*

Dorwald F. A. Side Reactions in Organic Synthesis, 2005, Wiley: VCH, Weinheim p. IX of Preface & p. 41.*

John F. Hartwig "Palladium-Catalyzed Amination of Aryl Halides and Sulfonates" in Modern Arene Chemistry. Edited by Didier Astruc, Wiley-VCH Weinheim 2002, pp. 107-168.*

Horchler, C. L. et. al "Synthesis of novel quinolone and quinoline-2-carboxylic acid 4-morpholin-4-yl-phenyl)amides: A late-stage diversification approach to potent 5HT1B antagonists" Bioorganic & Medicinal Chemistry 2007, 15, 939-950.*

See Dudash et. al. "Synthesis and evaluation of 3-anilino-quinoxalinones as glycogen phosphorylase inhibitors" Bioorganic & Medicinal Chemistry Letters 2005, 15, 4790-4793.*

Martin, Yvonne C. et. al. "Do Structurally Similar Molecules Have Similar Biological Activity?" Journal of Medicinal Chemistry 2002, 45, 4350-4358.*

Borisy et. al. "Systematic discovery of multicomponent therapeutics" PNAS 2003, 100, 7977-7982.*

Grant R. Zimmermann "Multi-target therapeutics: when the whole is greater than the sum of the parts." Drug Discovery Today 2007, 12, 34-42.*

Yan, Ligang et. al. "Synthesis and antibacterial activity of 7-substituted-1-ethyl(2-fluoro-ethyl)-6,8-difluoro-1,4-dihydro-4-oxo-quinoline-3-carboxylic acid." Yaoxue Xuebao, 1998, 33(5), 392-395.*

Asakawa, A., et al., Cocaine-Amphetamine-Regulated Transcript Influences Energy Metabolism, Anxiety and Gastric Emptying in Mice, Hormone and Metabolic Research, 2001, vol. 33(9), pp. 554-558.

Drueckes P et al., Photometric Microtiter Assay of Inorganic Phosphate in the Presence of Acid-Labile Organic Phosphates, Anal. Biochem, 1995, vol. 230(1), pp. 173-177.

Engers H. D. et al., Kinetic Mechanism of Phosphorylase a. I. Initial Velocity Studies, Biochem Jul. 1970 vol. 48(7), pp. 746-754.

Lee Daniel W., et al., Leptin Agonists As A Potential Approach To The Treatment Of Obesity, Drugs Of The Future, (2001), vol. 26, No. 9, pp. 873-881.

Link, H., et. al., 266. Abkommli9nge der 3-Chinolincarbonsaure mit Sauerstoffsubstitution in Stellung 4,5 und 8: Synthese, Reaktionen, NMR.-Studien, Helvetica Chimica Acta—vol. 65, Fase.8 (1982)—Nr.266 pp. 2645-2667.

Martin W. et al, Discovery of a human liver glycogen phosphorylase inhibitor that lowers blood glucose in vivo, Proceedings of the National Academy of Sciences of USA, vol. 95, Feb. 1998, pp. 1776-1781.

Salvador Javier et al., Perspectives in the Therapeutic Use of Leptin, Expert Opinion Pharmacotherapy, (2001), vol. 2, No. 10, pp. 1615-1622.

Tyle, Praveen, Iontophoretic Devices for Drug Delivery, Pharmaceutical Research, vol. 3, No. 6, 1986 pp. 318-326.

Wolfe, et. al., Rational Developement of Practical Catalysis for Aromatic Carbon-Nitrogen Bond Formation, Acc. Chem. Res. (1998) vol. 31 pp. 805-818.

Zunft, H. et al., Carob Pulp Preparation for Treatment of Hypercholesterolemia, Advances in Therapy, 2001, vol. 18(5), pp. 230-236.

* cited by examiner

HETEROCYCLICALLY SUBSTITUTED 7-AMINO-4-QUINOLONE-3-CARBOXYLIC ACID DERIVATIVES, PROCESS FOR THEIR PREPARATION AND THEIR USE AS MEDICAMENTS

Heterocyclically substituted 7-amino-4-quinolone-3-carboxylic derivatives, process for their preparations and their use as medicaments.

The invention relates to heterocyclically substituted 7-amino-7-4-quinolone-3-carboxylic acid derivatives and to the physiologically functional derivatives thereof.

Compounds of similar structure have already been described in the art (Link, Helmut; Bernauer, Karl; Englert Gerhard, Helvetica Chimica Acta 65(8), 1982, 2645-2667).

The invention was based on the object of providing compounds which display a therapeutically usable blood glucose-lowering effect.

The invention therefore relates to compounds of the formula I

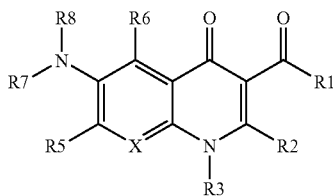

in which the meanings are
R1 OH, O—($C_1$-$C_6$)-alkyl or O—($C_1$-$C_6$)—OCO—($C_1$-$_6$)-alkyl;
R2 H, ($C_1$-$C_6$)-alkyl or phenyl;
R3 H, ($C_1$-$C_8$)-alkyl, ($C_3$-$C_7$)-cycloalkyl, pyridyl or phenyl, where alkyl may be substituted by R9 and where pyridyl or phenyl may be substituted by R10;
R9 $NH_2$, NH—($C_1$-$C_6$)-alkyl, N—(($C_1$-$C_6$)-alkyl)$_2$, COOH, COO—($C_1$-$C_6$)-alkyl, ($C_3$-$C_7$)-cycloalkyl, heteroalkyl, heteroaryl, O-phenyl or phenyl, where phenyl and heteroaryl may be substituted by R11;
R10 F, Cl, Br, ($C_1$-$C_6$-alkyl), O—($C_1$-$C_6$)-alkyl, COOH, COO—($C_1$-$C_6$)-alkyl, $NH_2$, NH—($C_1$-$C_6$)-alkyl or N—(($C_1$-$C_6$)-alkyl)$_2$;
R11 F, Cl, ($C_1$-$C_6$-alkyl), O—($C_1$-$_6$)-alkyl, $NH_2$, NH—($C_1$-$C_6$)-alkyl, N—(($C_1$-$C_6$)-alkyl)$_2$, COOH or COO—($C_1$-$C_4$)-alkyl;
x C—R4 or N;
R4, R5, R6, independently of one another, H, F, Cl, Br, OH, $NO_2$, CN, ($C_1$-$C_6$)-alkyl or O—($C_1$-$C_6$)-alkyl, where alkyl may be substituted more than once by F, Cl or Br;
R7 H or ($C_1$-$C_6$)-alkyl;
R8 heterocycle, where the heterocycle may be substituted by ($C_1$-$C_4$)-alkyl, F, Cl, $CF_3$, COOH or COO—($C_1$-$C_4$)-alkyl;
and the physiologically tolerated salts thereof.

Preference is given to compounds of the formula I in which one or more radicals have the following meaning:
R1 OH, O—($C_1$-$C_6$)-alkyl or O—($C_1$-$C_6$)—OCO—($C_1$-$C_6$)-alkyl;
R2 H;
R3 H, ($C_1$-8)-alkyl, ($C_3$-$C_7$)-cycloalkyl, pyridyl or phenyl, where alkyl may be substituted by R9 and where pyridyl or phenyl may be substituted by R10;
R9 $NH_2$, NH—($C_1$-$C_6$)-alkyl, N—(($C_1$-$C_6$)-alkyl)$_2$, COOH, COO—($C_1$-$C_6$)-alkyl, ($C_3$-$C_7$)-cycloalkyl, heteroalkyl, heteroaryl, O-phenyl or phenyl, where phenyl and heteroaryl may be substituted by R11;
R10 F, Cl, Br, ($C_1$-$C_6$-alkyl), O—($C_1$-$C_6$)-alkyl, COOH, COO—($C_1$-$C_6$)-alkyl, $NH_2$, NH—($C_1$-$C_6$)-alkyl or N—(($C_1$-$C_6$)-alkyl)$_2$;
R11 F, Cl, ($C_1$-$C_6$-alkyl), O—($C_1$-$C_6$)-alkyl, $NH_2$, NH—($C_1$-$C_6$)-alkyl, N—(($C_1$-$C_6$)-alkyl)$_2$, COOH or COO—($C_1$-$C_4$)-alkyl;
X C—R4 or N;
R4, R5 independently of one another, H, F, Cl, Br, OH, $NO_2$, CN, ($C_1$-$C_6$)-alkyl or O—($C_1$-$C_6$)-alkyl, where alkyl may be substituted more than once by F, Cl or Br;
R6 H;
R7 H;
R8 heterocycle, where the heterocycle may be substituted by ($C_1$-$C_4$)-alkyl, F, Cl, $CF_3$, COOH or COO—($C_1$-$C_4$)-alkyl;
and the physiologically tolerated salts thereof.

Particular preference is given to compounds of the formula I in which one or more radicals have the following meaning:
R1 OH, O—($C_1$-$C_6$)-alkyl or O—($C_1$-$C_6$)—OCO—($C_1$-$C_6$)-alkyl;
R2 H;
R3 H, ($C_1$-$C_8$)-alkyl, ($C_3$-$C_7$)-cycloalkyl, pyridyl or phenyl, where alkyl may be substituted by R9 and where pyridyl or phenyl may be substituted by R10;
R9 $NH_2$, NH—($C_1$-$C_6$)-alkyl, N—(($C_1$-$C_6$)-alkyl)$_2$, COOH, COO—($C_1$-$C_6$)-alkyl, ($C_3$-$C_7$)-cycloalkyl, heteroalkyl, heteroaryl, O-phenyl or phenyl, where phenyl and heteroaryl may be substituted by R11;
R10 F, Cl, Br, ($C_1$-$C_6$-alkyl), O—($C_1$-$C_6$)-alkyl, COOH, COO—($C_1$-$C_6$)-alkyl, $NH_2$, NH—($C_1$-$C_6$)-alkyl or N—(($C_1$-$C_6$)-alkyl)$_2$;
R11 F, Cl, ($C_1$-$C_6$-alkyl), O—($C_1$-$C_6$)-alkyl, $NH_2$, NH—($C_1$-$C_6$)-alkyl, N—(($C_1$-$C_6$)-alkyl)$_2$, COOH or COO—($C_1$-$C_4$)-alkyl;
X C—R4 or N;
R4 H, F, Cl, Br, OH, $NO_2$, CN, ($C_1$-$C_6$)-alkyl or O—($C_1$-$C_6$)-alkyl, where alkyl may be substituted more than once by F, Cl or Br;
R5 H, F, Cl, Br, OH, $NO_2$, CN, ($C_1$-$C_6$)-alkyl or O—($C_1$-$C_6$)-alkyl, where alkyl may be substituted more than once by F, Cl or Br;
R6 H;
R7 H;
R8 a nitrogen-containing heterocycle, where the heterocycle may be substituted by ($C_1$-$C_4$)-alkyl, F, Cl, $CF_3$, COOH or COO—($C_1$-$C_4$)-alkyl;
and the physiologically tolerated salts thereof.

Very particular preference is given to compounds of the formula I in which one or more radicals have the following meaning:
R1 OH, O—($C_1$-$C_6$)-alkyl;
R2 H;
R3 H, ($C_1$-$C_8$)-alkyl, ($C_3$-$C_7$)-cycloalkyl, pyridyl or phenyl, where alkyl may be substituted by R9 and where pyridyl or phenyl may be substituted by R10;
R9 $NH_2$, NH—($C_1$-$C_6$)-alkyl, N—(($C_1$-$C_6$)-alkyl)$_2$, COOH, COO—($C_1$-$C_6$)-alkyl, ($C_3$-$C_7$)-cycloalkyl, heteroalkyl, heteroaryl, O-phenyl or phenyl, where phenyl and heteroaryl may be substituted by R11;
R10 F, Cl, Br, ($C_1$-$C_6$-alkyl), O—($C_1$-$C_6$)-alkyl, COOH, COO—($C_1$-$C_6$)-alkyl, $NH_2$, NH—($C_1$-$C_6$)-alkyl or N—(($C_1$-$C_6$)-alkyl)$_2$;
R11 F, Cl, ($C_1$-$C_6$-alkyl), O—($C_1$-$C_6$)-alkyl, $NH_2$, NH—($C_1$-$C_6$)-alkyl, N—(($C_1$-$C_6$)-alkyl)$_2$, COOH or COO—($C_1$-$C_4$)-alkyl;
X C—R4 or N;
R4 H, F, Cl, Br, OH, $NO_2$, CN, ($C_1$-$C_6$)-alkyl or O—($C_1$-$C_6$)-alkyl, where alkyl may be substituted more than once by F, Cl or Br;

R5 H, F, Cl, Br, OH, $NO_2$, CN, $(C_1-C_6)$-alkyl or O—$(C_1-C_6)$-alkyl, where alkyl may be substituted more than once by F, Cl or Br;

R6 H;

R7 H;

R8 a nitrogen-containing heterocycle which comprises one or two nitrogen atoms but no further heteroatoms, where the heterocycle may be substituted by $(C_1-C_4)$-alkyl, F, Cl, $CF_3$, COOH or COO—$(C_1-C_4)$-alkyl;

and the physiologically tolerated salts thereof.

The invention relates to compounds of the formula I in the form of their racemates, racemic mixtures and pure enantiomers and to their diastereomers and mixtures thereof.

Compounds of the formula I in which R8 is an aromatic heterocycle are preferred.

Compounds of the formula I in which R8 is an aromatic heterocycle comprising up to three nitrogen atoms are particularly preferred.

The alkyl radicals in the substituents R1, R2, R3, R4, R5, R6, R7, R8, R9, R10 and R11 may be both straight-chain and branched.

If radicals or substituents may occur more than once in the compounds of the formula I, they may all, independently of one another, have the stated meanings and be identical or different.

Pharmaceutically acceptable salts are, because their solubility in water is greater than that of the initial or basic compounds, particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts are ammonium salts, alkali metal salts (such as sodium and potassium salts), alkaline earth metal salts (such as magnesium and calcium salts), trometamol (2-amino-2-hydroxymethyl-1,3-propanediol), diethanolamine, lysine, or ethylenediamine.

Salts with a pharmaceutically unacceptable anion such as, for example, trifluoroacetate likewise belong within the framework of the invention as useful intermediates for the preparation or purification of pharmaceutically acceptable salts and/or for use in nontherapeutic, for example in vitro, applications.

As used herein, the following definitions will apply unless otherwise stated:

"Patient" means a warm blooded animal, such as for example rat, mice, dogs, cats, guinea pigs, and primates such as humans.

"Treat" or "treating" means to alleviate symptoms, eliminate the causation of the symptoms either on a temporary or permanent basis, or to prevent or slow the appearance of symptoms of the named disorder or condition.

"Therapeutically effective amount" means a quantity of the compound which is effective in treating the named disorder or condition.

"Pharmaceutically acceptable carrier" is a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

The citation of any reference herein should not be construed as an admission that such reference is available as "Prior Art" to the instant application.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

The term "physiologically functional derivative" used herein refers to any physiologically tolerated derivative of a compound of the formula I of the invention, for example an ester, which on administration to a mammal such as, for example, a human is able to form (directly or indirectly) a compound of the formula I or an active metabolite thereof.

Physiologically functional derivatives include prodrugs of the compounds of the invention. Such prodrugs can be metabolized in vivo to a compound of the invention. These prodrugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula I" hereinafter refer to compound(s) of the formula I as described above, and their salts, solvates and physiologically functional derivatives as described herein.

Heterocycle or heterocyclic radical means ring systems which, apart from carbon, also comprise heteroatoms such as, for example, nitrogen, oxygen or sulfur. This definition also includes ring systems in which the heterocycle or the heterocyclic radical is fused to benzene nuclei.

Suitable "heterocyclic rings" or "heterocyclic radicals" are acridinyl, azocinyl, benzimidazolyl, benzofuryl, benzothienyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, 2H,6H-1,5,2-dithiazinyl, dihydrofuro[2,3-b]tetrahydrofuran, furyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyrazolidinyl, pyrazolinyl, pyrazolyl, pyridazinyl, pyridooxazoles, pyridoimidazoles, pyridothiazoles, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, 6H-1,2,5-thiadazinyl, thiazolyl, 1,2,3-thiadiazolyl, 1,2,4-thiadiazolyl, 1,2,5-thiadiazolyl, 1,3,4-thiadiazolyl, thienyl, triazolyl, tetrazolyl and xanthenyl.

Pyridyl stands both for 2-, 3- and 4-pyridyl. Thienyl stands both for 2- and 3-thienyl. Furyl stands both for 2- and 3-furyl.

The corresponding N-oxides of these compounds are also included, that is to say, for example, 1-oxy-2-, 3- or 4-pyridyl.

Also included are derivatives of these heterocycles which are benzo-fused one or more times.

The heterocyclic rings or heterocyclic radicals may be substituted one or more times by suitable groups such as, for example: F, Cl, Br, I, $CF_3$, $NO_2$, $N_3$, CN, COOH, COO—$(C_1$-$C_6)$-alkyl, $CONH_2$, CONH—$(C_1$-$C_6)$-alkyl, $CON[(C_1$-$C_6)$-alkyl]$_2$, $(C_1$-$C_6)$-alkyl, $(C_2$-$C_6)$-alkenyl, $(C_2$-$C_6)$-alkynyl, O—$(C_1$-$C_6)$-alkyl, where one, more than one, or all hydrogen(s) in the alkyl radicals may be replaced by fluorine; $PO_3H_2$, $SO_3H$, $SO_2$—$NH_2$, $SO_2NH$—$(C_1$-$C_6)$-alkyl, $SO_2N[(C_1$-$C_6)$-alkyl]$_2$, S—$(C_1$-$C_6)$-alkyl, S—$(CH_2)_n$-phenyl, SO—$(C_1$-$C_6)$-alkyl, SO—$(CH_2)_n$-phenyl, $SO_2$—$(C_1$-$C_6)$-alkyl, $SO_2$—$(CH_2)_n$-phenyl, where n can be 0-6, and the phenyl radical may be substituted up to twice by F, Cl, Br, OH, $CF_3$, $NO_2$, CN, $OCF_3$, O—$(C_1$-$C_6)$-alkyl, $(C_1$-$C_6)$-alkyl, $NH_2$;

$C(NH)(NH_2)$, $NH_2$, NH—$(C_1$-$C_6)$-alkyl, $N((C_1$-$C_6)$-alkyl)$_2$, NH—$(C_1$-$C_7)$-acyl, phenyl, O—$(CH_2)_n$-phenyl, where n can be 0-6, and where the phenyl ring may be substituted one to 3 times by F, Cl, Br, I, OH, $CF_3$, $NO_2$, CN, $OCF_3$, O—$(C_1$-$C_6)$-alkyl, $(C_1$-$C_6)$-alkyl, $NH_2$, NH—$(C_1$-$C_6)$-alkyl $N((C_1$-$C_6)$-alkyl)$_2$, $SO_2$—$CH_3$, COOH, COO—$(C_1$-$C_6)$-alkyl or $CONH_2$.

The compound(s) of the formula (I) can also be administered in combination with further active ingredient.

The amount of a compound of formula I necessary to achieve the desired biological effect depends on a number of factors, for example the specific compound chosen, the intended use, the mode of administration and the clinical condition of the patient. The daily dose is generally in the range from 0.3 mg to 100 mg (typically from 3 mg and 50 mg) per day and per kilogram of bodyweight, for example 3-10 mg/kg/day. An intravenous dose may be, for example, in the range from 0.3 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampoules for injections may contain, for example, from 1 mg to 100 mg, and single-dose formulations which can be administered orally, such as, for example, tablets or capsules, may contain, for example, from 1.0 to 1000 mg, typically from 10 to 600 mg. For the therapy of the abovementioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units such as, for example, capsules, cachets, suckable tablets or tablets, each of which contain a defined amount of the compound of formula (I); as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one or more surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain a compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing a compound of the formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single plasters which are suitable for long-term close contact with the patient's epidermis. Such plasters suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

Further active ingredients suitable for combination products are:

all antidiabetics mentioned in the Rote Liste 2001, chapter 12. They may be combined with the compounds of the formula I of the invention in particular for a synergistic improvement of the effect. Administration of the active ingredient combination may take place either by separate administration of the active ingredients to the patient or in the form of combination products in which a plurality of active ingredients are present in one pharmaceutical preparation. Most of the active ingredients listed below are disclosed in the USP Dictionary of USAN and International Drug Names, US Pharmacopeia, Rockville 2001.

Antidiabetics include insulin and insulin derivatives such as, for example, Lantus® (see www.lantus.com) or HMR 1964, fast-acting insulins (see U.S. Pat. No. 6,221,633), GLP-1 derivatives such as, for example, those disclosed in WO 98/08871 of Novo Nordisk A/S, and orally effective hypoglycemic active ingredients.

The orally effective hypoglycemic active ingredients include, preferably, sulfonylureas, biguanidines, meglitinides, oxadiazolidinediones, thiazolidinediones, glucosidase inhibitors, glucagon antagonists, GLP-1 agonists, potassium channel openers such as, for example, those disclosed in WO 97/26265 and WO 99/03861 of Novo Nordisk A/S, insulin sensitizers, inhibitors of liver enzymes involved in the stimulation of gluconeogenesis and/or glycogenolysis, modulators of glucose uptake, compounds which alter lipid metabolism, such as antihyperlipidemic active ingredients and antilipidemic active ingredients, compounds which reduce food intake, PPAR and PXR agonists and active ingredients which act on the ATP-dependent potassium channel of the beta cells.

In one embodiment of the invention, the compounds of the formula I are administered in combination with an HMGCoA reductase inhibitor such as simvastatin, fluvastatin, pravastatin, lovastatin, atorvastatin, cerivastatin, rosuvastatin.

In one embodiment of the invention, the compounds of the formula I are administered in combination with a cholesterol absorption inhibitor such as, for example, ezetimibe, tiqueside, pamaqueside.

In one embodiment of the invention, the compounds of the formula I are administered in combination with a PPAR gamma agonist, such as, for example, rosiglitazone, pioglitazone, JTT-501, G1 262570.

In one embodiment of the invention, the compounds of the formula I are administered in combination with PPAR alpha agonist, such as, for example, GW 9578, GW 7647.

In one embodiment of the invention, the compounds of the formula I are administered in combination with a mixed PPAR alpha/gamma agonist, such as, for example, GW 1536, AVE 8042, AVE 8134, AVE 0847, or as described in PCT/US 11833, PCT/US 11490, DE10142734.4.

In one embodiment of the invention, the compounds of the formula I are administered in combination with a fibrate such as, for example, fenofibrate, clofibrate, bezafibrate.

In one embodiment of the invention, the compounds of the formula I are administered in combination with an MTP inhibitor such as, for example, implitapide, BMS-201038, R-103757.

In one embodiment of the invention, the compounds of the formula I are administered in combination with bile acid absorption inhibitor (see, for example, U.S. Pat. No. 6,245,744 or U.S. Pat. No. 6,221,897), such as, for example, HMR 1741.

In one embodiment of the invention, the compounds of the formula I are administered in combination with a CETP inhibitor, such as, for example, JTT-705.

In one embodiment of the invention, the compounds of the formula I are administered in combination with a polymeric bile acid adsorbent such as, for example, cholestyramine, colesevelam.

In one embodiment of the invention, the compounds of the formula I are administered in combination with an LDL receptor inducer (see U.S. Pat. No. 6,342,512), such as, for example, HMR1171, HMR1586.

In one embodiment of the invention, the compounds of the formula I are administered in combination with an ACAT inhibitor, such as, for example, avasimibe.

In one embodiment of the invention, the compounds of the formula I are administered in combination with an antioxidant, such as, for example, OPC-14117.

In one embodiment of the invention, the compounds of the formula I are administered in combination with a lipoprotein lipase inhibitor, such as, for example, NO-1886.

In one embodiment of the invention, the compounds of the formula I are administered in combination with an ATP-citrate lyase inhibitor, such as, for example, SB-204990.

In one embodiment of the invention, the compounds of the formula I are administered in combination with a squalene synthetase inhibitor, such as, for example, BMS-188494.

In one embodiment of the invention, the compounds of the formula I are administered in combination with a lipoprotein (a) antagonist, such as, for example, CI-1027 or nicotinic acid.

In one embodiment of the invention, the compounds of the formula I are administered in combination with a lipase inhibitor, such as, for example, orlistat.

In one embodiment of the invention, the compounds of the formula I are administered in combination with insulin.

In one embodiment, the compounds of the formula I are administered in combination with a sulfonylurea such as, for example, tolbutamide, glibenclamide, glipizide or glimepiride.

In one embodiment, the compounds of the formula I are administered in combination with a biguanide, such as, for example, metformin.

In one further embodiment, the compounds of the formula I are administered in combination with a meglitinide, such as, for example, repaglinide.

In one embodiment, the compounds of the formula I are administered in combination with a thiazolidinedione, such as, for example, troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]phenyl]methyl]-2,4-thiazolidinedione.

In one embodiment, the compounds of the formula I are administered in combination with an α-glucosidase inhibitor, such as, for example, miglitol or acarbose.

In one embodiment, the compounds of the formula I are administered in combination with an active ingredient which acts on the ATP-dependent potassium channel of the beta cells, such as, for example, tolbutamide, glibenclamide, glipizide, glimepiride or repaglinide.

In one embodiment, the compounds of the formula I are administered in combination with more than one of the aforementioned compounds, e.g. in combination with a sulfonylurea and metformin, with a sulfonylurea and acarbose, repaglinide and metformin, insulin and a sulfonylurea, insulin and metformin, insulin and troglitazone, insulin and lovastatin, etc.

In a further embodiment, the compounds of the formula I are administered in combination with CART modulators (see "Cocaine-amphetamine-regulated transcript influences energy metabolism, anxiety and gastric emptying in mice" Asakawa, A, et al., M.: Hormone and Metabolic Research (2001), 33(9), 554-558), NPY antagonists, e.g. naphthalene-1-sulfonic acid {4-[(4-aminoquinazolin-2-ylamino)methyl]cyclohexylmethyl}amide; hydrochloride (CGP 71683A)), MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxoethyl]-amide; (WO 01/91752)), orexin antagonists (e.g. 1-(2-methylbenzoxazol-6-yl)-3-[1,5]naphthyridin-4-ylurea; hydrochloride (SB-334867-A)), H3 agonists (3-cyclohexyl-1-(4,4-dimethyl-1,4,6,7-tetrahydroimidazo[4,5-c]pyridin-5-yl)propan-1-one oxalic acid salt (WO 00/63208)); TNF agonists, CRF antagonists (e.g. [2-methyl-9-(2,4,6-trimethylphenyl)-9H-1,3,9-triazafluoren-4-yl]dipropylamine (WO 00/66585)), CRF BP antagonists (e.g. urocortin), urocortin agonists, β3 agonists (e.g. 1-(4-chloro-3-methanesulfonylmethylphenyl)-2-[2-(2,3-dimethyl-1H-indol-6-yloxy)-ethylamino]-ethanol hydrochloride (WO 01/83451)), MSH (melanocyte-stimulating hormone) agonists, CCK-A agonists (e.g. {2-[4-(4-chloro-2,5-dimethoxyphenyl)-5-(2-cyclohexyl-ethyl)thiazol-2-ylcarbamoyl]-5,7-dimethylindol-1-yl}acetic acid trifluoroacetic acid salt (WO 99/15525)), serotonin reuptake inhibitors (e.g. dexfenfluramine), mixed sertoninergic and noradrenergic compounds (e.g. WO 00/71549), 5HT agonists e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (6-benzyloxy-1-(2-diisopropylaminoethylcarbamoyl)-3,4-dihydro-1H-isoquinoline-2-carboxylic acid tert-butyl ester (WO 01/85695)), TRH agonists (see, for example, EP 0 462 884), uncoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881), DA agonists (bromocriptine, Doprexin), lipase/amylase inhibitors (e.g. WO 00/40569), PPAR modulators (e.g. WO 00/78312), RXR modulators or TR-β agonists.

In one embodiment of the invention, the other active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment, the other active ingredient is dexamphatamine or amphetamine.

In one embodiment, the other active ingredient is fenfluramine or dexfenfluramine.

In another embodiment, the other active ingredient is sibutramine.

In one embodiment, the other active ingredient is orlistat.

In one embodiment, the other active ingredient is mazindol or phentermine.

In one embodiment, the compounds of the formula I are administered in combination with bulking agents, preferably insoluble bulking agents (see, for example, carob/Caromax® (Zunft H J; et al., Carob pulp preparation for treatment of hypercholesterolemia, ADVANCES IN THERAPY (2001 September-October), 18(5), 230-6.) Caromax is a carob-containing product from Nutrinova, Nutrition Specialties & Food Ingredients GmbH, Industriepark Höchst, 65926 Frankfurt/Main)). Combination with Caromax® is possible in one preparation or by separate administration of compounds of the formula I and Caromax®. Caromax® can in this connection also be administered in the form of food products such as, for example, in bakery products or muesli bars.

It will be appreciated that every suitable combination of the compounds of the invention with one or more of the aforementioned compounds and optionally one or more further pharmacologically active substances will be regarded as falling within the protection conferred via the present invention.

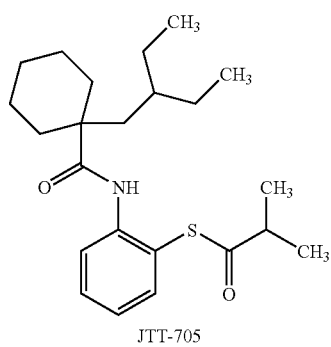
JTT-705

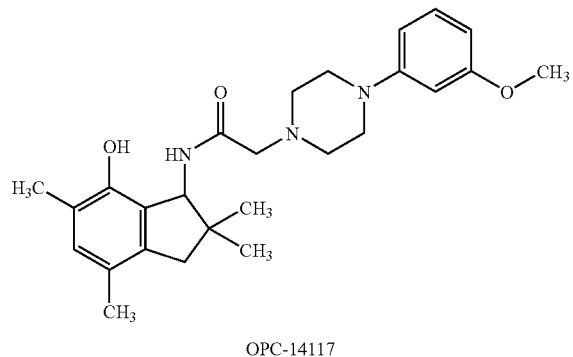
OPC-14117

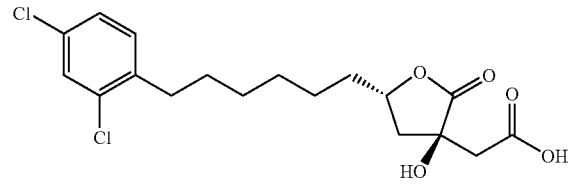
SB-204990

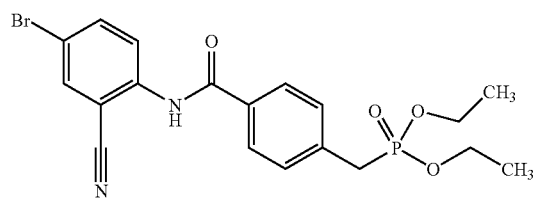
NO-1886

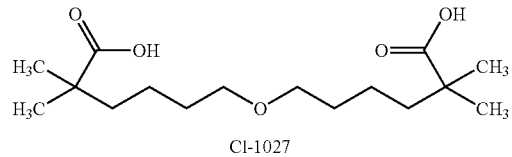
CI-1027

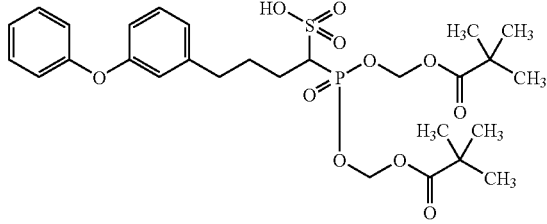
BMS-188494

-continued

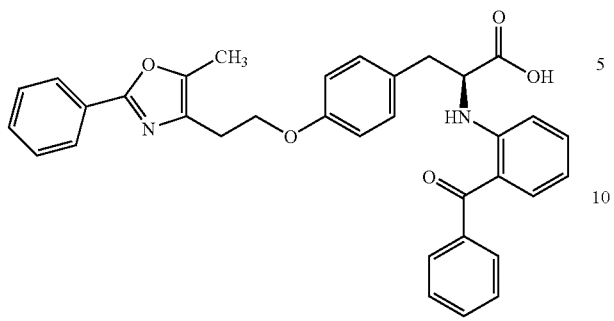

GI 262570

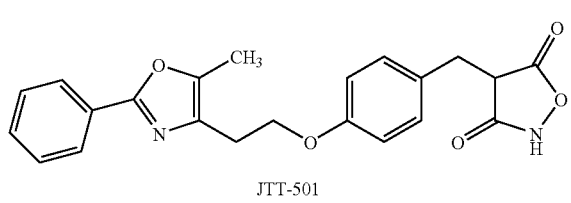

JTT-501

Preparation of the compounds of the formula I is described in the following schemes: Compounds of the formula II can be reacted under Buchwald conditions with amines of the formula III to give compounds of the formula IV in which R8 does not correspond to pyrrol-1-yl and R1' has the meaning of an ester. In this case, Y is Br, I or triflate. With these Buchwald conditions it is possible to employ catalyst systems with Pd(OAc)$_2$ or Pd$_2$(dba)$_3$ as palladium sources, BINAP, xanthphos and DPPF as ligands and Cs$_2$CO$_3$, K$_3$PO$_4$ or NaO$^t$Bu as bases. Solvents which can be used are, for example, toluene, DME, dioxane, TIF or DMF. The reaction conditions may be chosen from conventional heating or heating and reaction in a microwave. (Literature: Buchwald, *Acc. Chem. Res.* 1998, 31, 805) Optional subsequent hydrolysis of the compounds of the formula IV and optional conversion to different amides or esters leads to compounds of the formula I.

Scheme 1:

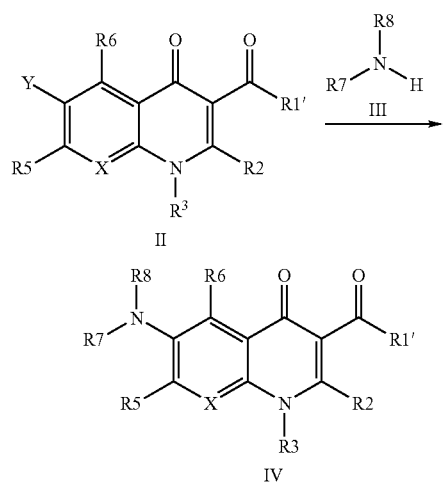

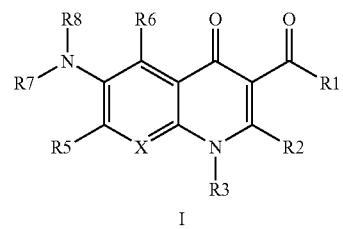

I

Compounds of the formula I in which R8 corresponds to pyrrol-1-yl can be prepared by reacting compounds of the formula II in which Y is fluorine or bromine with hydrazine and subsequent reaction with diketo compounds of the formula V to give compounds of the formula VI, subsequent ester cleavage and optional conversion to different amides or esters.

Scheme 2:

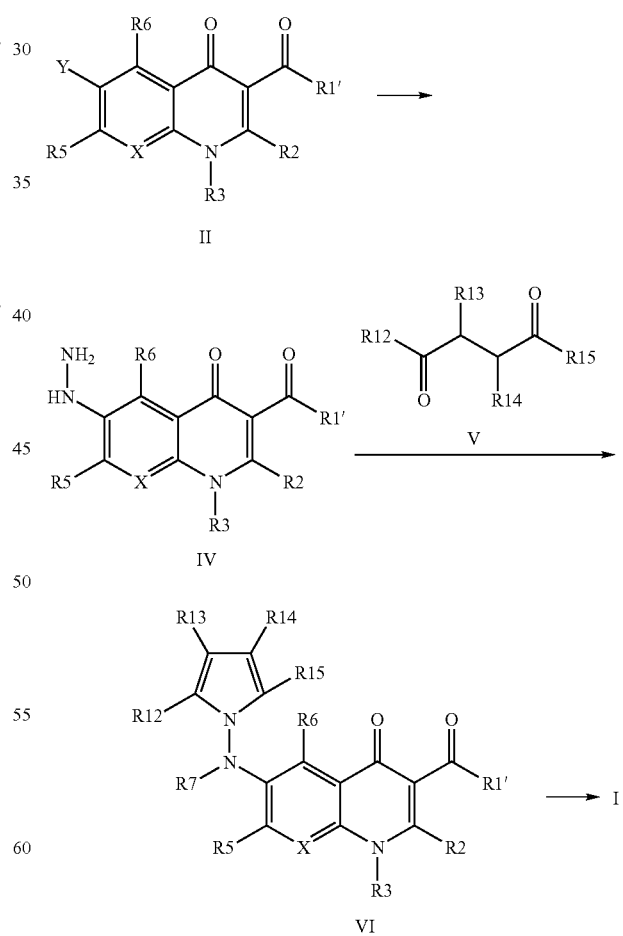

The examples listed below serve to illustrate the invention but without restricting it.

TABLE 1

| Example | R1 | R2 | R3 | X | R5 | R6 | R7 | R8 | Salt |
|---|---|---|---|---|---|---|---|---|---|
| 1 | OEt | H | Et | N | Me | H | H | 6-oxo-pyridin-3-yl | — |
| 2 | OEt | H | Et | N | Me | H | H | 2-methyl-6-(trifluoromethyl)pyridin-3-yl | — |
| 3 | OEt | H | Et | N | Me | H | H | 6-fluoropyridin-3-yl | — |
| 4 | OEt | H | Et | N | Me | H | H | 6-ethylpyridin-2-yl | — |
| 5 | OEt | H | Et | N | Me | H | H | 5-oxo-pyridin-2-yl | — |
| 6 | OEt | H | Et | N | Me | H | H | 4-methylpyrimidin-2-yl | — |
| 7 | OEt | H | Et | N | Me | H | H | 4-methylpyridin-2-yl | — |
| 8 | OEt | H | Et | N | Me | H | H | pyridin-3-yl | — |

TABLE 1-continued
| Example | R1 | R2 | R3 | X | R5 | R6 | R7 | R8 | | Salt |
|---------|-----|----|----|---|----|----|----|----|----|------|
| 9 | OH | H | Et | N | Me | H | H | 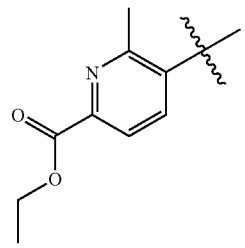 | | — |
| 10 | OEt | H | Et | N | Me | H | H | 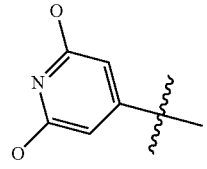 | | — |
| 11 | OH | H | Et | N | Me | H | H | 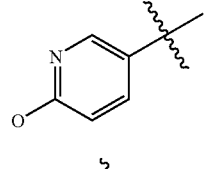 | | — |
| 12 | OEt | H | Et | N | Me | H | H | 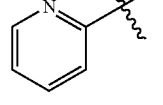 | | — |
| 13 | OEt | H | Et | N | Me | H | H | 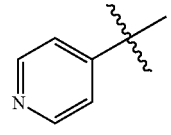 | | — |
| 14 | OEt | H | Et | N | Me | H | H | 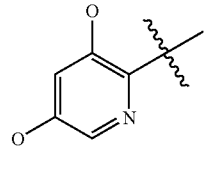 | | — |
| 15 | OEt | H | Et | N | Me | H | H | 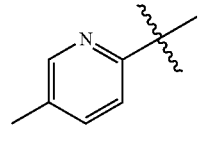 | | — |
| 16 | OEt | H | Et | N | Me | H | H | 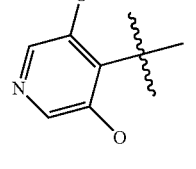 | | — |

TABLE 1-continued
| Example | R1 | R2 | R3 | X | R5 | R6 | R7 | R8 | Salt |
|---|---|---|---|---|---|---|---|---|---|
| 17 | OEt | H | Et | N | Me | H | H | 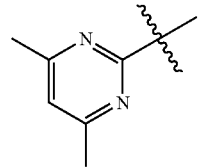 | — |
| 18 | OH | H | Et | N | Me | H | H | 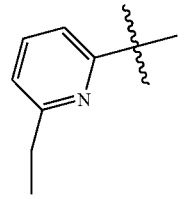 | — |
| 19 | OH | H | Et | N | Me | H | H | 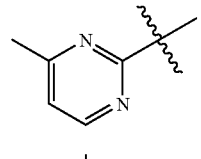 | — |
| 20 | OEt | H | Et | N | Me | H | H | 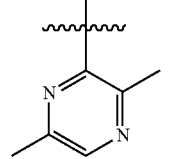 | TFA |
| 21 | OEt | H | Et | N | Me | H | H | 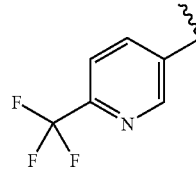 | TFA |
| 22 | OEt | H | Et | N | Me | H | H | 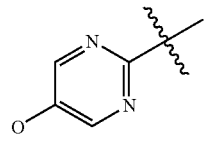 | TFA |
| 23 | OH | H | Et | N | Me | H | H | 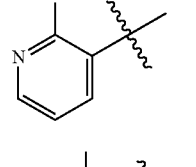 | — |
| 24 | OH | H | Et | N | Me | H | H | 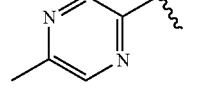 | — |

TABLE 1-continued

[Structure: naphthyridinone core with substituents R1 (C(=O)R1 at 3-position), R2, R3 (N1), X, R5, R6, R7, R8 (N-R7R8 at 6-position)]

| Example | R1 | R2 | R3 | X | R5 | R6 | R7 | R8 | (R8 group) | Salt |
|---|---|---|---|---|---|---|---|---|---|---|
| 25 | OH | H | Et | N | Me | H | H | | 5-(2-trifluoromethyl)pyridinyl | — |
| 26 | OH | H | Et | N | Me | H | H | | 3-(4-trifluoromethyl)pyridinyl | TFA |
| 27 | OH | H | Et | N | Me | H | H | | 6-methyl-2-carboxy-pyridin-5-yl | — |
| 28 | OEt | H | Et | N | Me | H | H | | 2-oxo-pyridin-3-yl | TFA |
| 29 | OH | H | Et | N | Me | H | H | | pyridin-3-yl | — |
| 30 | OH | H | Et | N | Me | H | H | | 5-methyl-pyridin-2-yl | — |
| 31 | OH | H | Et | N | Me | H | H | | 4,6-dimethyl-pyrimidin-2-yl | — |

TABLE 1-continued
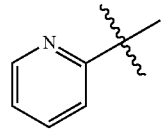
| Example | R1 | R2 | R3 | X | R5 | R6 | R7 | R8 | Salt |
|---|---|---|---|---|---|---|---|---|---|
| 32 | OH | H | Et | N | Me | H | H | 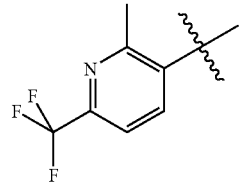 | — |
| 33 | OH | H | Et | N | Me | H | H | 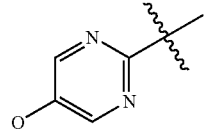 | — |
| 34 | OH | H | Et | N | Me | H | H | 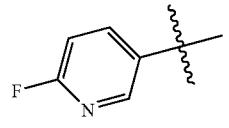 | TFA |
| 35 | OH | H | Et | N | Me | H | H | 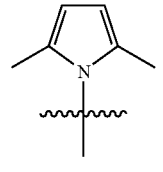 | — |
| 36 | OH | H | Et | CH | Cl | H | H | 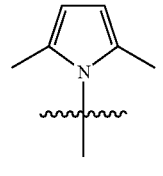 | — |
| 37 | OH | H | Et | CH | Cl | H | H | 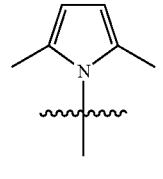 | TRIS |
| 38 | OEt | H | Et | CH | H | H | H | 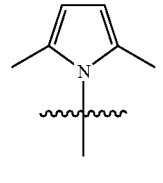 | — |
| 39 | OMe | H | Et | CH | H | H | H |  | — |

TABLE 1-continued
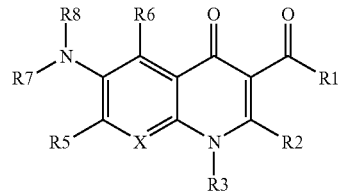
| Example | R1 | R2 | R3 | X | R5 | R6 | R7 | R8 | Salt |
|---|---|---|---|---|---|---|---|---|---|
| 40 | OH | H | Me | CH | Cl | H | H | 2,5-dimethylpyrrol-1-yl | — |
| 41 | OH | H | Me | CH | Cl | H | H | 2,5-dimethylpyrrol-1-yl | TRIS |
| 42 | OH | H | benzyl | CH | Cl | H | H | 2,5-dimethylpyrrol-1-yl | — |
| 43 | OH | H | cyclopropyl | CH | Cl | H | H | 2,5-dimethylpyrrol-1-yl | — |
| 44 | OH | H | cyclopropyl | CH | Cl | H | H | 2,5-dimethylpyrrol-1-yl | TRIS |
| 45 | OH | H | n-Pr | CH | Cl | H | H | 2,5-dimethylpyrrol-1-yl | — |
| 46 | OH | H | n-Pr | CH | Cl | H | H | 2,5-dimethylpyrrol-1-yl | TRIS |

TABLE 1-continued
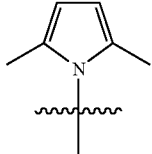
| Example | R1 | R2 | R3 | X | R5 | R6 | R7 | R8 | Salt |
|---|---|---|---|---|---|---|---|---|---|
| 47 | OH | H | n-Bu | CH | Cl | H | H | 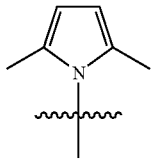 | — |
| 48 | OH | H | Et | CH | H | H | Me | 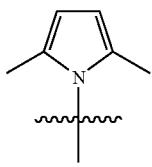 | — |
| 49 | OH | H | Et | CH | H | H | H | 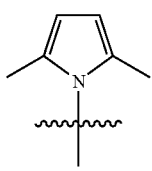 | — |
| 50 | OH | H | Et | C—OMe | H | H | H | 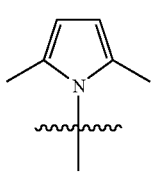 | — |
| 51 | OH | H | Et | CH | CF3 | H | H | 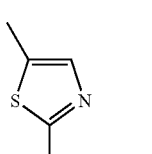 | — |
| 52 | OMe | H | Et | C—Me | H | H | H | 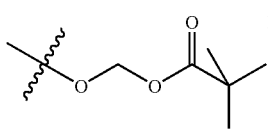 | — |
| 53 | 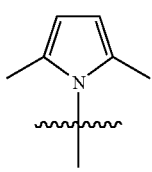 | H | Et | CH | Cl | H | H |  | — |

TABLE 1-continued

| Example | R1 | R2 | R3 | X | R5 | R6 | R7 | R8 | Salt |
|---|---|---|---|---|---|---|---|---|---|
| 54 | OMe | H | Et | C—Me | H | H | H | 4-methylthiazol-2-yl | — |
| 55 | OMe | H | Et | C—Me | H | H | H | pyridin-4-yl | — |
| 56 | OMe | H | Et | C—Me | H | H | H | 3-methylpyridin-2-yl | — |
| 57 | OH | H | Et | C—Me | H | H | H | pyridin-4-yl | — |
| 58 | OMe | H | Et | C—Me | H | H | H | pyridin-3-yl | — |
| 59 | OMe | H | Et | C—Me | H | H | H | 6-methylpyridin-2-yl | — |
| 60 | OMe | H | Et | C—Me | H | H | H | pyrimidin-2-yl | — |

TABLE 1-continued

| Example | R1 | R2 | R3 | X | R5 | R6 | R7 | R8 | Salt |
|---|---|---|---|---|---|---|---|---|---|
| 61 | OH | H | Et | C—Me | H | H | H | 6-methylpyridin-2-yl | — |
| 62 | OH | H | Et | C—Me | H | H | H | 3-methylpyridin-2-yl | — |
| 63 | OH | H | Et | C—Me | H | H | H | pyrimidin-2-yl | — |
| 64 | OEt | H | Et | C—Me | H | H | H | pyrazin-2-yl | — |
| 65 | OH | H | Et | C—Me | H | H | H | pyrazin-2-yl | — |
| 66 | OH | H | Et | C—Me | H | H | H | pyridin-2-yl | — |

TABLE 1-continued
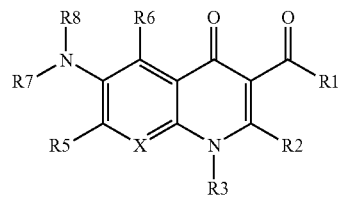
| Example | R1 | R2 | R3 | X | R5 | R6 | R7 | R8 | Salt |
|---|---|---|---|---|---|---|---|---|---|
| 67 | OMe | H | Et | C—Me | H | H | H | 5-(trifluoromethyl)pyridin-2-yl | — |
| 68 | OMe | H | Et | C—Me | H | H | H | 6-fluoropyridin-3-yl | — |
| 69 | OMe | H | Et | C—Me | H | H | H | 2-methyl-6-(trifluoromethyl)pyridin-3-yl | — |
| 70 | OMe | H | Et | C—Me | H | H | H | 4-methylpyridin-2-yl | — |
| 71 | OH | H | Et | C—Me | H | H | H | 4-methylpyridin-2-yl | — |
| 72 | OMe | H | Et | C—Me | H | H | H | 2,6-dioxo-1,2,3,6-tetrahydropyridin-3-yl | TFA |

TABLE 1-continued
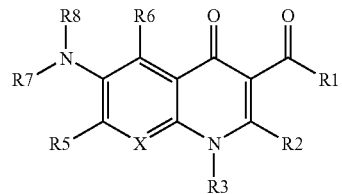
| Example | R1 | R2 | R3 | X | R5 | R6 | R7 | R8 | Salt |
|---|---|---|---|---|---|---|---|---|---|
| 73 | OMe | H | Et | C—Me | H | H | H | 3,6-dimethylpyrazin-2-yl | TFA |
| 74 | OMe | H | Et | C—Me | H | H | H | 5-oxo-pyrimidin-2-yl | TFA |
| 75 | OH | H | Et | C—Me | H | H | H | 2-oxo-pyridin-3-yl | TFA |
| 76 | OH | H | Et | C—Me | H | H | H | 2,6-dioxo-pyridin-3-yl | TFA |
| 77 | OH | H | Et | C—Me | H | H | H | 3,6-dimethylpyrazin-2-yl | TFA |
| 78 | OH | H | Et | C—Me | H | H | H | 4-trifluoromethyl-pyridin-3-yl | TFA |
| 79 | OH | H | Et | C—Me | H | H | H | 5-oxo-pyrimidin-2-yl | TFA |
| 80 | OMe | H | Et | Me | H | H | H | piperidin-1-yl | — |

The activity of the compounds was assayed as follows:
Glycogen phosphorylase a Activity Assay The effect of compounds on the activity of the active form of glycogen phosphorylase (GPa) was measured in the reverse direction by following the synthesis of glycogen from glucose 1-phosphate by determining the liberation of inorganic phosphate. All the reactions were carried out as duplicate determinations in microtiter plates with 96 wells (Half Area Plates, Costar No 3696), measuring the change in absorption owing to the formation of the reaction product at the wavelength specified hereinafter in a Multiskan Ascent Elisa Reader (Lab Systems, Finland).

In order to measure the GPa enzymic activity in the reverse direction, the general method of Engers et al. (Engers H D, Shechosky S, Madsen N B, Can J Biochem 1970 July; 48(7): 746-754) was used to measure the conversion of glucose 1-phosphate into glycogen and inorganic phosphate, with the following modifications: human glycogen phosphorylase a (for example with 0.76 mg of protein/ml (Aventis Pharma Deutschland GmbH), dissolved in buffer solution E (25 mM β-glycerophosphate, pH 7.0, 1 mM EDTA and 1 mM dithiothreitol) was diluted with buffer T (50 mM Hepes, pH 7.0, 100 mM KCl, 2.5 mM EDTA, 2.5 mM $MgCl_2.6H_2O$) and addition of 5 mg/ml glycogen to a concentration of 10 μg of protein/ml. Test substances were prepared as 10 mM solution in DMSO and diluted to 50 μM with buffer solution T. To 10 μl of this solution were added 10 μl of 37.5 mM glucose, dissolved in buffer solution T, and 5 mg/mL glycogen, plus 10 μl of a solution of human glycogen phosphorylase a (10 μg of protein/ml) and 20 μl of glucose 1-phosphate, 2.5 mM. The baseline glycogen phosphorylase a activity in the absence of test substance was determined by adding 10 μl of buffer solution T (0.1% DMSO). The mixture was incubated at room temperature for 40 minutes, and the liberated inorganic phosphate was measured by the general method of Drueckes et al. (Drueckes P, Schinzel R, Palm D, *Anal Biochem* 1995 Sep. 1;230(1): 173-177) with the following modifications: 50 μl of a stop solution of 7.3 mM ammonium molybdate, 10.9 mM zinc acetate, 3.6% ascorbic acid, 0.9% SDS are added to 50 μl of the enzyme mixture. After incubation at 45° C. for 60 minutes, the absorption at 820 nm was measured. To determine the background absorption, in a separate mixture the stop solution was added immediately after addition of the glucose 1-phosphate solution.

This test was carried out with a concentration of 10 μM of the test substance in order to determine the particular inhibition of glycogen phosphorylase a in vitro by the test substance.

TABLE 2

Biological activity

| Ex. | % inhibition at 10 μM |
|---|---|
| 3 | 11 |
| 5 | 9 |
| 9 | 5 |
| 10 | 81 |
| 18 | 16 |
| 24 | 37 |
| 26 | 55 |
| 34 | 40 |
| 35 | 91 |
| 41 | 98 |
| 42 | 101 |
| 44 | 99 |
| 46 | 97 |
| 47 | 99 |
| 48 | 32 |
| 50 | 98 |
| 51 | 96 |
| 53 | 93 |
| 57 | 26 |
| 60 | 4 |
| 68 | 14 |

It is evident from the table that the compounds of the formula I inhibit the activity of glycogen phosphorylase a and are thus very suitable for lowering the blood glucose level.

The preparation of some examples is described in detail below, and the other compounds of the formula I were obtained analogously:

Experimental Part:

EXAMPLE 42 a) 1-Benzyl-7-chloro-6-hydrasino-4-oxo-1,4-dihydroquinolone-3-carboxylic acid

A suspension of 154 mg of 1-benzyl-7-chloro-6-fluoro-4-oxo-1,4-dihydroquinolone-3-carboxylic acid, 3 ml of N-methylpyrrolidone and 0.12 ml of hydrazine hydrate was heated at 110° C. with stirring for 3.5 hours. After cooling to 5° C., the resulting precipitate was filtered off with suction and washed with diethyl ether and acetone, and the crude mixture was reacted in the next stage without further purification.
Yield: 70% b) 1-Benzyl-7-chloro-6-(2,5-dimethylpyrrol-1-ylamino)-4-oxo-1,4-dihydroquinolone-3-carboxylic acid A solution of 111 mg of 1-benzyl-7-chloro-6-hydrazino-4-oxo-1,4-dihydroquinolone-3-carboxylic acid, 1.42 ml of glacial acetic acid, 75 μl of hexanedione and 8 ml of ethanol was heated at 80° C. for 2 hours. The reaction mixture was evaporated to dryness in a rotary evaporator. The pure product was isolated from the crude mixture by chromatography on an HPLC system. A Merck Purospher-RP18 column and, as eluent, an acetonitrile: water mixture was used for this; the initial acetonitrile content was 30% and rose to 60% over the course of 20 minutes.
Yield 8%

Examples 36-41 and 43-51 were obtained analogously.

EXAMPLE 53

2,2-Dimethylpropionyloxymethyl 7-chloro-6-(2,5-dimethylpyrrol-1-ylamino)-1-ethyl-4-oxo-1,4-dihydroquinolone-3-carboxylate 18 μl of 1,8-diazabicyclo[5.4.0]undec-7-ene were added to a solution of 21 mg of 7-chloro-6-(2,5-dimethylpyrrol-1-ylamino)-1-ethyl-4-oxo-1,4-dihydroquinolonecarboxylic acid (Example 36) in 3 ml of acetonitrile and stirred at room temperature for 30 minutes. Then 36 μl of chloromethyl pivalate were added, and reaction was allowed to take place at room temperature for 5 days. The resulting precipitate was filtered off with suction to afford 3.3 mg of pure product.

EXAMPLE 56

Methyl 1-ethyl-8-methyl-6-(3-methylpyridin-2-ylamino)-4-oxo-1,4-dihydroquinolone-3-carboxylate 100 mg of methyl 6-bromo-1-ethyl-8-methyl-4-oxo-1,4-dihydroquinolone-3-carboxylate were transferred together with 40 mg of 2-amino-3-methylpyridine, 20 mg of Pd(OAc)$_2$, 60 mg of XANTPHOS and 250 mg of cesium carbonate into a suitable reaction vessel, a protective gas atmosphere was generated with argon, and 10 ml of dioxane were added. The mixture was then heated at 80° C. for 8 h. The pure product was isolated from the reaction solution by chromatography on an HPLC system. This entailed use of a Merck Purospher RP-18 column and an acetonitrile:water mixture as eluent; the initial acetonitrile content was 15% and rose to 95% over the course of 20 minutes.

Yield: 23%

Examples 1-8, 10, 12-17, 20-22, 28, 52, 54-56, 58-60, 64, 67-70, 72-74 and 80 were obtained in an analogous way. The yields varied between 10 and 30%.

EXAMPLE 62

1-Ethyl-8-methyl-6-(3-methylpyridin-2-ylamino)-4-oxo-1,4-dihydroquinolone-3-carboxylic acid Methyl 1-ethyl-6-(4-methoxy-2-methylphenylamino)-8-methyl-4-oxo-1,4-dihydroquinolone-3-carboxylate (30 mg) was dissolved in 5 ml of dioxane, 2.5 equivalents of a 1 N NaOH solution were added, and the mixture was heated at 60° C. for 4 h. Removal of the solvent in vacuo was followed by chromatography on an HPLC system to purify the product. The pure product was isolated from the reaction solution by chromatography on an HPLC system. This entailed use of a Merck Purospher-RP18 column and an acetonitrile:water mixture as eluent; the initial acetonitrile content was 15% and rose to 95% over the course of 20 minutes.

Yield: 75%

Examples 9, 11, 18-19, 23-27, 29-35, 57, 61-63, 65-66, 71 and 75-79 were obtained in an analogous way.

What is claimed is:

1. A compound of the formula I

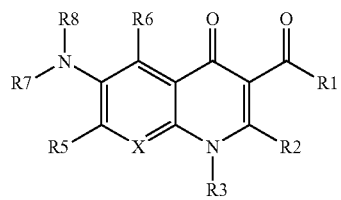

in which the meanings are

R1 is OH or O—($C_1$-$C_6$)-alkyl;
R2 is H or ($C_1$-$C_6$)-alkyl;
R3 is ($C_1$-$C_8$)-alkyl, ($C_3$-$C_7$)-cycloalkyl or benzyl;
X is N;
R4 is H, ($C_1$-$C_6$)-alkyl or O—($C_1$-$C_6$)-alkyl;
R5 is H, F, Cl, Br, $CF_3$ or ($C_1$-$C_6$)-alkyl;
R6 is H;
R7 is H or ($C_1$-$C_6$)-alkyl;
R8 is pyridine, thiazole, pyrazine, pyrimidine or pyrrole;
and the physiologically tolerated salts thereof.

2. The compound of claim 1 wherein
R1 is OH or O—($C_1$-$C_6$)-alkyl;
R2 is H;
R3 is ($C_1$-$C_8$)-alkyl, ($C_3$-$C_7$)-cycloalkyl or benzyl;
X is N;
R4 is H, ($C_1$-$C_8$)-alkyl or O—($C_1$-$C_6$)-alkyl;
R5 is H, F, Cl, Br, $CF_3$ or ($C_1$-$C_6$)-alkyl;
R6 is H;
R7 is H;
R8 is pyridine, thiazole, pyrazine, pyrimidine or pyrrole;
and the physiologically tolerated salts thereof.

3. The compound of claim 1 wherein
R1 is OH or O—($C_1$-$C_6$)-alkyl;
R2 is H;
R3 is ($C_1$-$C_8$)-alkyl, ($C_3$-$C_7$)-cycloalkyl or benzyl;
X is N;
R4 is H, ($C_1$-$C_6$)-alkyl or O—($C_1$-$C_6$)-alkyl;
R5 is H, F, Cl, Br, $CF_3$, or —($C_1$-$C_6$)-alkyl;
R6 is H;
R7 is H;
R8 is pyridine, thiazole, pyrazine, pyrimidine or pyrrole;
and the physiologically tolerated salts thereof.

4. The compound of claim 1 wherein
R1 is OH, O—($C_1$-$C_6$)-alkyl;
R2 is H;
R3 is ($C_1$-$C_8$)-alkyl, ($C_3$-$C_7$)-cycloalkyl or benzyl;
X is N;
R4 is H, ($C_1$-$C_6$)-alkyl or O—($C_1$-$C_6$)-alkyl;
R5 is H, F, Cl, Br, $CF_3$, or ($C_1$-$C_6$)-alkyl;
R6 is H;
R7 is H;
R8 is pyridine, thiazole, pyrazine, pyrimidine or pyrrole;
and the physiologically tolerated salts thereof.

5. A pharmaceutical composition comprising one or more compounds of claim 1 and a pharmaceutically acceptable carrier.

* * * * *